United States Patent [19]

Tomioka et al.

[11] Patent Number: 5,057,102
[45] Date of Patent: Oct. 15, 1991

[54] CONTRAST ADJUSTOR FOR AIMING LASER

[75] Inventors: Yuko Tomioka; Hiroshi Koizumi; Masatsugu Kijima, all of Tokyo, Japan

[73] Assignee: Kabushiki Kaisha Topcon, Japan

[21] Appl. No.: 524,876

[22] Filed: May 18, 1990

[30] Foreign Application Priority Data

May 29, 1989 [JP] Japan ................................. 1-132707

[51] Int. Cl.$^5$ .............................................. A61N 5/06
[52] U.S. Cl. .................................. 606/004; 606/012; 128/395
[58] Field of Search ............... 128/395, 397, 398, 897; 351/206, 214; 606/4–6, 10–19; 354/62

[56] References Cited

U.S. PATENT DOCUMENTS

| | | | |
|---|---|---|---|
| 4,316,467 | 2/1982 | Macherheide | 606/9 |
| 4,409,979 | 10/1983 | Roussel et al. | 606/17 |
| 4,644,948 | 2/1987 | Lang et al. | 606/4 |
| 4,648,892 | 3/1987 | Kittrell et al. | 606/7 |
| 4,741,612 | 5/1988 | Berngruber et al. | 606/4 |
| 4,768,513 | 9/1988 | Suzuki | 606/9 |
| 4,917,486 | 4/1990 | Raven | 606/4 |

Primary Examiner—David Shay
Attorney, Agent, or Firm—Lorusso & Loud

[57] ABSTRACT

A laser treatment apparatus is to treat a site of disease of a patient with a laser beam. The laser treatment apparatus contains a source of illumination light for irradiating a site of treatment of the patient and a site around the site of treatment with the illumination light; a source of aiming light for irradiating the site of treatment with the aiming light; a light-receiving device for receiving a light reflected from an aiming site to which the aiming light is applied and from a site around the aiming site; a setting means for comparing a ratio of a quantity of light reflected from the aiming site, as received by the light-receiving means, to a quantity of light reflected from the site around the aiming site with a predetermined ratio; and a control unit for controlling an illuminance of the aiming light with respect to the illumination light by adjusting a ratio of the quantity of light reflected from the aiming site to the quantity of light reflected from the site around the aiming site so as to reach a predetermined ratio.

6 Claims, 3 Drawing Sheets

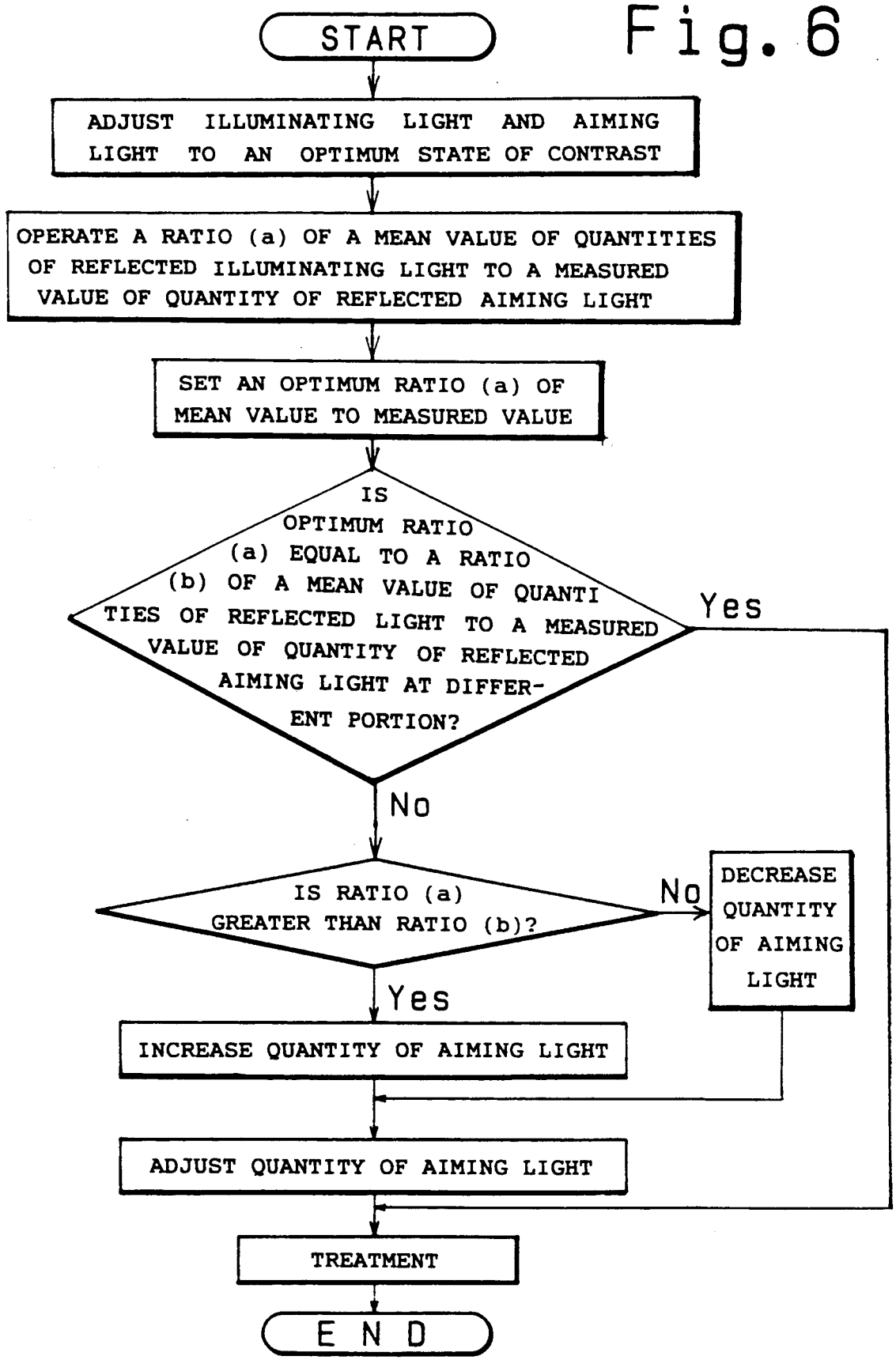

CONTRAST ADJUSTOR FOR AIMING LASER

BACKGROUND OF THE INVENTION

1. Field of the Invention

The present invention relates to a laser treatment apparatus and, more particularly, to a laser treatment apparatus for treating a site of disease of a patient by irradiation with laser beams.

2. Description of Related Art

For conventional laser treatment apparatuses, visual brightness of an aiming light for aiming at a target of laser beams may vary with a site of observation because a reflectance of the aiming light varies with the site of observation. The brightness of the aiming light also may vary with a change in a magnification of observation or in a size of a spot of the aiming light.

The aiming light is applied, for example, to a site of treatment, i.e., a site of observation of the eyeground, together with laser beams. And an entire area of the eyeground is illuminated with an illumination means. If the contrast or illuminance of the aiming light with respect to a light of illumination around the aiming light would be low, the operator has the difficulty in observing the illumination light, thereby failing to allow the laser beams to be applied to the correct site of observation and resulting in surgical accidents. Hence, conventional laser treatment apparatuses require the operator to adjust the optimum quantity of the aiming light by observing the site of observation under illumination with the aiming light whenever operation is to be performed.

SUMMARY OF THE INVENTION

Therefore, the present invention has the object to provide a laser treatment apparatus adapted to allow the operator to readily observe the aiming light while keeping the visual brightness of the aiming light.

In order to achieve the object, the present invention consists of a laser treatment apparatus for treating a site of disease of a patient with a laser beam, comprising:

a source of illumination light for irradiating a site of treatment of the patient and a site around the site of treatment with the illumination light;

a source of aiming light for irradiating the site of treatment with the aiming light;

a light-receiving means for receiving a light reflected from an aiming site to which the aiming light is applied and from a site around the aiming site;

a setting means for comparing a ratio of a quantity of light reflected from the aiming site, as received by the light-receiving means, to a quantity of light reflected from the site around the aiming site with a predetermined ratio; and a control unit for controlling an illuminance of the aiming light with respect to the illumination light by adjusting a ratio of the quantity of light reflected from the aiming site to the quantity of light reflected from the site around the aiming site so as to reach a predetermined ratio.

BRIEF DESCRIPTION OF THE DRAWINGS

FIG. 6 is a flow chart showing adjustment of a ratio concerning a quantity of light reflected.

DETAILED DESCRIPTION OF THE PREFERRED EMBODIMENTS

Figure 1:
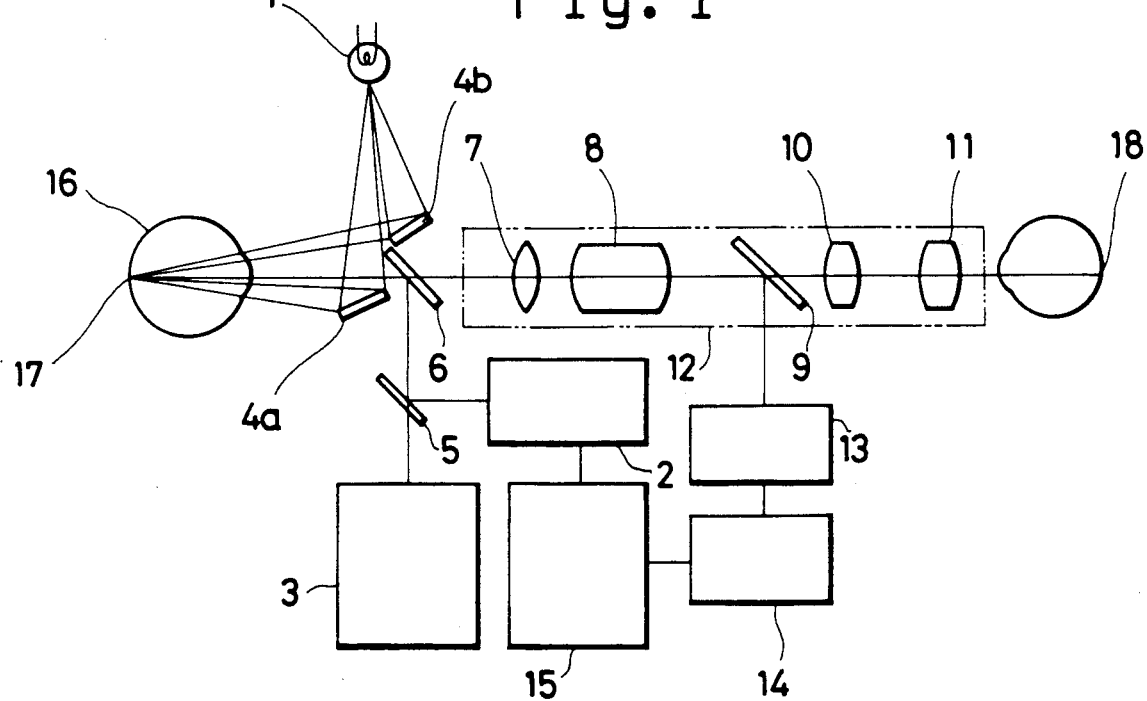
FIG. 1 is a schematic diagram of the laser treatment apparatus according to an embodiment of the present invention.

As shown in FIG. 1, reference numeral 1 denotes a source of light for illumination for applying a light of illumination to a site of treatment of a patient and a site around the site of treatment and reference numeral 2 denotes a source of aiming light for aiming the light at a site of treatment. The light-receiving means 13 is to receive light reflected from the aimed portion illuminated by the aiming light and a light reflected from the portion around the aiming site. The setting unit 14 is to compare a ratio of a quantity of the light reflected from the aimed portion, as received by the light-receiving means, to the predetermined ratio.

The control unit 15 is to control the illuminance of the aiming light with respect to light for illumination by allowing the setting unit to adjust the ratio of the quantity of light reflected from the aimed portion to the quantity of light reflected from the portion around the aimed portion.

The laser treatment apparatus of the present invention will be described by taking a photocoagulator for use in the field of ophthalmology as an example.

Operation of the vitreous in the eye is made, for example, to replace a turbid vitreous in the form of a gel present between the lens and the retina by a transparent liquid by absorbing the vitreous, thereby allowing the light to pass through the lens and reach the retina and recovering vision.

During this operation, the retinal lacuna may be treated. i.e., the disease site such as retinal lacuna at the posterior pole of the eyeball is closed by means of photocoagulation. This photocoagulation operation is made, for example, by applying laser beams to a site of disease through optical fibers while observing this site by means of an operational microscope.

Illuminating Light Source 1

A light of illumination from the illuminating light source 1 is designed to be reflected from divided reflection mirrors 4a and 4b so as to illuminate the entire portion of the eyeground 17 of the eye of a patient. It is to be noted as a matter of course that the entire portion of the eyeground 17 contains the site of treatment and the site around the site of treatment, as will be described hereinafter. As the light source 1 for illumination may be used a white light source such as tungsten lamp and so on.

Aiming Light Source 2

The aiming light source 2 generates an aiming light to the site of treatment which is photocoagulated by irradiating the site of treatment with laser beams. The aiming light is applied to the site of treatment of the eyeground 17 of the eye 16 of the patient by reflecting the light in a half mirror 5 and a half mirror 6. As the aiming light source 2 may be used He-Ne laser and LEDs of visible light.

Light Source 3 for Laser Beams

The light source 3 for laser beams may include, for example, high-power semiconductor lasers. The laser beams may be designed to reach the eyeground 17 by passing through the half mirror 5 and reflecting in the half mirror 6. The laser beams are irradiated on the optical axis parallel to and identical to that of the aiming light that aims at the position of irradiation for the laser beams.

Observation Optics 12

The aiming light is illuminating the site of treatment of the eyeground 17, and the aiming light reflected from the eyeground 17 is observed through observation optics 12, together with the light for illumination reflected from the eyeground 17 illuminated. The observation optics 12 comprises an object lens 7, a zoom lens 8, an image lens 10 and an eyepiece 11. The state of the eyeground 17 of the eye 16 of a person undergoing optical examination is grasped through the observation optics 12 by the eye 18 of an examiner.

Detector 13 as a Light-Receiving Means

A detector 13 is disposed in a position coordinate optically with the eye 18 of the examiner behind the zoom lens 8 of the observation optics 12 in order to receive the light reflected from the aimed portion illuminated with the aiming light and from the portion in the vicinity of the aimed portion. In other words, the distance between a half mirror 9 and the eyeground of the eye 18 of the examiner is set so as to be equal to the distance between the half mirror and the detector 13.

Figure 2:
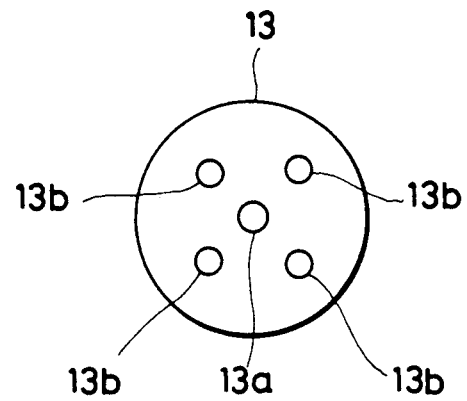
FIG. 2 is a view showing a light-receiving unit of the detector.
Figure 3:
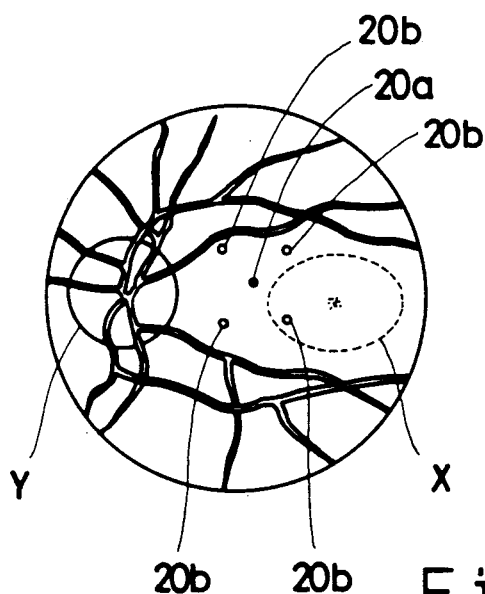
FIG. 3 shows the treatment site 20a and the four reference sites 20b.
Figure 4:
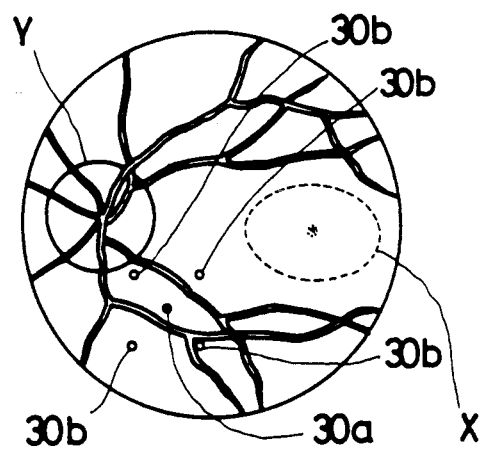
FIG. 4 shows the treatment site 30a and the four reference sites 30b.
Figure 5:
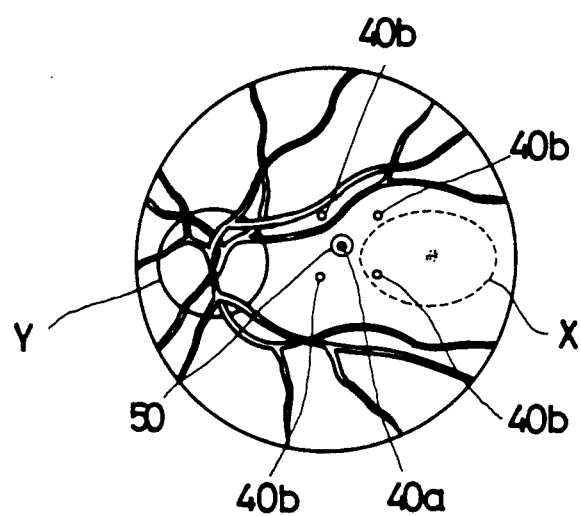
FIG. 5 shows the treatment site 40a and the four reference sites 40b.

Turning to FIG. 2, the detector 13 is designed such that light-receiving elements 13a and 13b are disposed so as to correspond to each of positions as shown in FIGS. 3, 4 and 5, i.e., an aiming point 20a and points of illumination 20b as shown in FIG. 3, an aiming point 30a and points of illumination 30b as shown in FIG. 4 and an aiming point 40a and points of illumination 40b as shown in FIG. 5. As shown in FIG. 2, the light-receiving element 13a is located in the central position of the detector 13 and four of the light-receiving elements 13b are located each in an equal distance away from the light-receiving element 13a so as to enclose the light-receiving element 13a.

More specifically, the light-receiving element 13a of FIG. 2 is disposed so as to correspond to the aiming point 20a as shown in FIG. 3 and four of the light-receiving elements 13b of FIG. 2 are disposed so as to correspond to the respective points 20b for illumination as shown in FIG. 3.

The light-receiving element 13a of FIG. 2 is disposed so as to correspond to the central point 30a for aiming as shown in FIG. 4 and four of the light-receiving elements 13b of FIG. 2 are disposed so as to correspond to the respective points 30b for illumination as shown in FIG. 4.

The light-receiving element 13a of FIG. 2 is disposed so as to correspond to the central point 40a for aiming as shown in FIG. 5 and four of the light-receiving elements 13b of FIG. 2 are disposed so as to correspond to the respective points 40b for illumination as shown in FIG. 5. It is to be noted herein that FIG. 5 represents the case wherein the diameter of a spot of the aiming light in the aiming point 40a is greater than the diameter of a spot of the aiming light in the aiming point 20a as shown in FIG. 3.

The light-receiving element 13a is disposed so as to receive the aiming light reflected from the aiming point 20a, 30a or 40b that is the site of treatment as shown in FIG. 3, 4 or 5, respectively, while the light-receiving elements 13b are disposed so as to receive the illumination light reflected from the illumination points 20b, 30b or 40b that are disposed in the portions in the vicinity of the site of treatment, as shown in FIG. 3, 4 or 5, respectively.

It is noted herein that FIGS. 3 to 5 are images obtained by directly observing the eyegrounds of the left eyes of different persons. The region as indicated by reference symbol "X" represents the macular reflection ring. The region as indicated by reference symbol "Y" represents the optic disk.

Setting Unit 14

The setting unit 14 is to compare the ratio of the quantity of light reflected from the aimed point, which is detected by the detector 13, to the quantity of light reflected from the illumination point with a predetermined optimum ratio. For the setting unit 14, the operator sets the optimum ratio of the quantity of light reflected from the site of treatment of the eyeground, as being suitable for observation, to the quantity of light reflected from the portion around the site of treatment.

The result of a comparison of the ratio detected by the detector 13 with the optimum ratio is fed to the control unit 15 which, in turn, controls the aiming light source 2 on the basis of the comparison result. In other words, the control unit 15 adjusts the ratio of the quantity of light reflected from the aimed portion to the quantity of light reflected from the portion around the aimed portion so as to reach the optimum ratio.

The aimed light so adjusted is then applied from the aiming light source 2 through the half mirror 5 and the half mirror 6 to the eyeground 17 of the eye 16 of the person undergoing optical examination.

Reference is made to FIG. 6.

Setting of Optimum Ratio at First Site of Treatment

Description will be made of the setting of the optimum ratio by the setting unit.

The operator applies the aiming light to the aiming point 20a while applying the light for illumination to four of the illumination points 20b, as shown in FIG. 3. The intensity of brightness for the aiming light is then adjusted by controlling the control unit 15 by operating the setting unit 14 as shown in FIG. 1, thereby providing an optimum contrast of the light for illumination light with respect to the light aimed at.

As the optimum contrast is obtained, the detector 13 as shown in FIG. 1 produces a mean value of the quantities of light reflected from the four illumination points 20b and measures the quantity of the aimed light reflected from the aimed point 20a.

Then, the setting unit 14 operates a ratio (a) of the mean value of the quantities of light reflected from the four illumination points 20b to the measured value of the quantity of the aiming light reflected from the aimed point 20a. This ratio (a) is stored by the setting unit 14 as an optimum ratio (a reference value).

With the arrangement as described hereinabove, the visually optimum light for aiming is applied to the aiming point 20a as shown in FIG. 3, thereby permitting the application of laser beams to the site for treatment and making a laser operation.

Setting of Optimum Ratio at Another Site for Treatment

As shown in FIG. 4, the aimed point 30a is a site for treatment to be operated with laser beams.

In this case, the detector 13 is arranged so as to obtain a ratio (b) of a mean value among the quantities of light reflected from four of illumination points 30b to a measured value of the quantity of the aiming light reflected from the aimed point 30a.

The setting unit 14 then compares the optimum ratio (a) with the ratio (b) obtained hereinabove.

When it is found that the ratio (a) is equal to the ratio (b), it is decided that the aiming light is applied with an optimum contrast to the site for treatment so that the eyeground is treated.

If the ratio (a) is found to be greater than the ratio (b), the brightness of the aiming light lacks so that the quantity of the aiming light is increased by controlling the source 2 for the aiming light by means of the control unit 15. And the laser operation at the aiming point (site of treatment) is started when the ratio (a) reaches the ratio (b). If the ratio (a) is found to be smaller than the ratio (b), on the contrary, the brightness of the aiming light is so excessive that the quantity of the aiming light is decreased by controlling the source 2 for the aiming light by means of the control unit 15. And the laser operation at the aimed point (site of treatment) is started when the ratio (a) reaches the ratio (b).

As seen from the embodiment described hereinabove, the present invention allows the operator to observe the eyeground with an optimum illuminance, which can always be set prior to treatment, even if a site for treatment would provide a different ratio of the quantity of light reflected from the aimed point to the quantity of light reflected from the illumination points. Hence, an error in the site for treatment or in applying a treating light can be avoided, thereby improving safety of treatment to a great extent.

It is to be noted herein that FIGS. 3 and 4 indicate the spot of the laser light in the same size as that of the aimed points 20a and 30a, respectively. FIG. 5 indicates the spot of aiming light 50 in a size greater than the spot size of the laser light. In other words, the aiming light 50 having a spot size greater than that of the laser light is applied to the aimed point 40a.

In this case, too, there are obtained a ratio (c) of a mean value of quantities of light reflected from the illumination points 40b to a measured value of the quantity of the aiming light reflected from the aimed point 40a, and this ratio (c) is compared with the optimum ratio.

As described hereinabove, even if laser light having a spot in different size is applied, there can be optimized a ratio of the amount of aiming light to be likewise applied to the amount of illumination light. This can permit observation in an optimum contrast and improve safety of treatment.

When the magnification of observation is changed, the aiming light can be observed in an optimum contrast by obtaining a ratio of a mean value of the quantities of reflected illumination light to a measured value of the quantity of reflected aiming light and comparing this ratio with the optimum ratio.

The present invention may be embodied in other specific forms without departing from the spirit and scope thereof. The present embodiments as have been described hereinabove are therefore to be considered in all respects as illustrative and not restrictive, the scope of the invention being indicated by the appended claims, and all the changes, modifications and variations which come within the meaning and range of equivalency of the claims are therefore intended to be encompassed within the spirit and scope of the invention.

What is claimed is:

1. A laser treatment apparatus for treating a site of disease of a patient with a laser beam, comprising:

a source of illumination light including means for irradiating a site of treatment of the patient and a site around the site of treatment with the illumination light;

a source of aiming light including means for irradiating the site of treatment with the aiming light;

light-receiving means for receiving a light reflected from an aiming site to which the aiming light is applied and from a site around the aiming site;

a setting means for comparing a ratio of a quantity of light reflected from the aiming site, as received by the light-receiving means, to a quantity of light reflected from the site around the aiming site with a predetermined ratio; and a control unit including means for controlling an illuminance of the aiming light with respect to the illumination light by adjusting a ratio of the quantity of light reflected from the aiming site to the quantity of light reflected from the site around the aiming site so as to reach a predetermined ratio.

2. A laser treatment apparatus as claimed in claim 1, wherein said source of illumination comprises a white light source.

3. A laser treatment apparatus as claimed in claim 1, wherein the source of aiming light is a helium-neon laser or a visible light emitting diode.

4. A laser treatment apparatus as claimed in claim 1, wherein the laser beam is applied along an optical axis which is coincident with that of the aiming light.

5. A laser treatment apparatus as claimed in claim 1, wherein the light-receiving means comprises a detector having a light-receiving element corresponding to a point reflecting the aiming light and a plurality of light-receiving elements corresponding to points reflecting the illumination light.

6. A laser treatment apparatus as claimed in claim 5, wherein the detector includes means for obtaining a mean value of intensity of light reflected to the plurality of light-receiving elements and a value of intensity of light reflected to the light-receiving element corresponding to the point of the aiming light.

* * * * *